United States Patent
Pruitt et al.

(10) Patent No.: US 9,138,567 B2
(45) Date of Patent: Sep. 22, 2015

(54) CONTROLLING CATHETER FLOW

(71) Applicant: Covidien LP, Mansfield, MA (US)

(72) Inventors: Sean Pruitt, Franklin, MA (US); Brent Marsden, Reading, MA (US)

(73) Assignee: Covidien LP, Mansfield, MA (US)

( * ) Notice: Subject to any disclaimer, the term of this patent is extended or adjusted under 35 U.S.C. 154(b) by 100 days.

(21) Appl. No.: 13/792,376

(22) Filed: Mar. 11, 2013

(65) Prior Publication Data

US 2014/0257243 A1  Sep. 11, 2014

(51) Int. Cl.
| | |
|---|---|
| *A61M 25/00* | (2006.01) |
| *A61M 25/10* | (2013.01) |
| *A61M 1/36* | (2006.01) |
| *A61L 29/04* | (2006.01) |
| *A61L 29/06* | (2006.01) |
| *A61L 29/16* | (2006.01) |

(52) U.S. Cl.
CPC .......... *A61M 25/1002* (2013.01); *A61L 29/042* (2013.01); *A61L 29/06* (2013.01); *A61L 29/16* (2013.01); *A61M 1/3653* (2013.01); *A61M 25/003* (2013.01); *A61M 25/0074* (2013.01); *A61L 2300/404* (2013.01); *A61L 2300/42* (2013.01); *A61M 25/007* (2013.01); *A61M 2025/0031* (2013.01); *A61M 2025/0079* (2013.01)

(58) Field of Classification Search
CPC .......... A61M 25/007; A61M 25/0075; A61M 2025/0037; A61M 25/003; A61M 25/0074; A61M 25/0071; A61M 25/0073; A61M 25/10; A61M 2025/1093

USPC ............ 604/96.01, 103.05, 167.03, 246, 256
See application file for complete search history.

(56) References Cited

U.S. PATENT DOCUMENTS

| | | | | |
|---|---|---|---|---|
| 2,819,718 | A | * | 1/1958 | Goldman ................. 604/103.09 |
| 2,919,697 | A | | 1/1960 | Kim |
| 3,788,326 | A | * | 1/1974 | Jacobs ..................... 128/207.15 |
| 3,863,641 | A | * | 2/1975 | Popa .............................. 604/267 |
| 4,186,745 | A | * | 2/1980 | Lewis et al. ................... 604/265 |
| 4,285,341 | A | | 8/1981 | Pollack |
| 4,610,665 | A | * | 9/1986 | Matsumoto et al. ..... 604/167.04 |
| 5,053,023 | A | | 10/1991 | Martin |
| 5,188,595 | A | * | 2/1993 | Jacobi ........................... 604/509 |
| 5,360,403 | A | | 11/1994 | Mische |

(Continued)

OTHER PUBLICATIONS

Extended Search Report from counterpart European Patent Application No. 14154892.5, dated Sep. 24, 2014, 7 pp.

(Continued)

*Primary Examiner* — Kevin C Sirmons
*Assistant Examiner* — William Carpenter
(74) *Attorney, Agent, or Firm* — John Paul Mello, Esq.

(57) ABSTRACT

A catheter assembly includes an elongate member and a balloon. The elongate member defines at least one lumen and an outer surface. The outer surface defines at least one opening in fluid communication with the at least one lumen. The balloon is disposed within the at least one lumen. The balloon is inflatable such that a portion of the balloon expands from the at least lumen through the at least one opening. The expansion of the balloon increases the flow restriction through the at least one opening compared to the flow restriction through the at least one opening when the balloon is in a deflated condition. Methods for using a catheter assembly to remove occlusive material from a catheter are also described.

11 Claims, 5 Drawing Sheets

(56) References Cited

U.S. PATENT DOCUMENTS

| | | | |
|---|---|---|---|
| 5,549,551 A * | 8/1996 | Peacock et al. | 604/103.05 |
| 5,618,266 A * | 4/1997 | Liprie | 604/21 |
| 5,792,118 A | 8/1998 | Kurth et al. | |
| 5,807,329 A * | 9/1998 | Gelman | 604/102.03 |
| 6,045,531 A * | 4/2000 | Davis | 604/101.05 |
| 6,074,374 A | 6/2000 | Fulton | |
| 6,270,489 B1 * | 8/2001 | Wise et al. | 604/508 |
| 6,299,599 B1 * | 10/2001 | Pham et al. | 604/113 |
| 6,599,316 B2 * | 7/2003 | Vardi et al. | 623/1.15 |
| 6,692,459 B2 | 2/2004 | Teitelbaum | |
| 7,799,064 B2 * | 9/2010 | Brucker et al. | 623/1.11 |
| 8,152,951 B2 | 4/2012 | Zawacki et al. | |
| 2002/0016584 A1 | 2/2002 | Wise et al. | |
| 2004/0181191 A1 | 9/2004 | Teitelbaum | |
| 2008/0208307 A1 * | 8/2008 | Ben-Muvhar et al. | 623/1.11 |
| 2008/0221655 A1 * | 9/2008 | Miller | 623/1.11 |
| 2009/0264822 A1 * | 10/2009 | Johnson | 604/103.07 |
| 2012/0330231 A1 * | 12/2012 | Pruitt et al. | 604/103.02 |
| 2013/0324964 A1 | 12/2013 | Florescu | |

OTHER PUBLICATIONS

Eureka Medical, "Balloon Embolectomy Catheter", http://www.eurekamed.com/balloon-embolectomy-catheter.html, Sep. 17. 2012, 3 pages, 2004.

Edwards Lifesciences Corporation. "Fogarty Cathers", 3 pages, 2010.

* cited by examiner

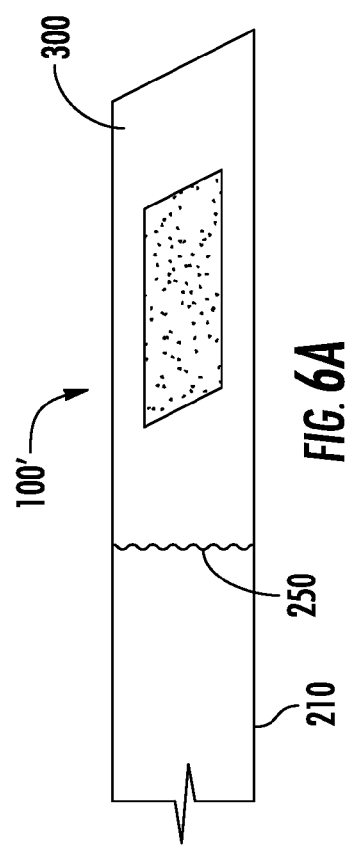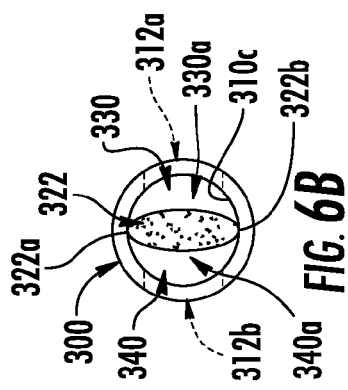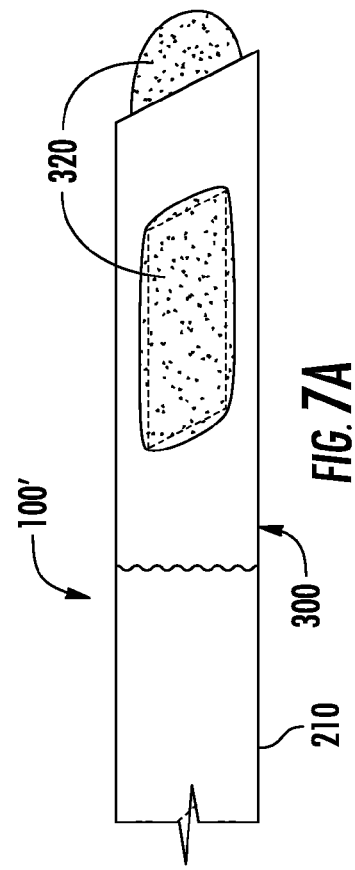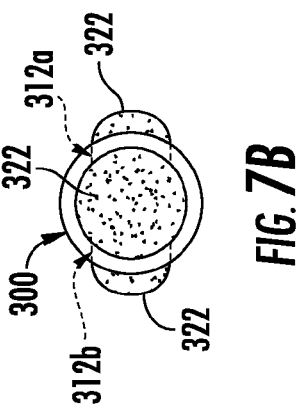

CONTROLLING CATHETER FLOW

TECHNICAL FIELD

The present disclosure generally relates to catheter assemblies, and more particularly, to controlling flow through catheter assemblies.

BACKGROUND

Catheters are flexible medical instruments that facilitate withdrawal and introduction of fluids from and to body cavities, ducts, and vessels. Catheters may have particular application, for example, in a hemodialysis procedure where blood is withdrawn from a blood vessel for treatment, and subsequently returned to the blood vessel for circulation. During some hemodialysis procedures, a multiple lumen catheter is inserted into a body and blood is withdrawn through an arterial lumen of the catheter. The removed blood is directed, via extension tubes, to a hemodialysis machine which dialyzes, or purifies, the blood to remove waste and toxins. The purified blood is then returned through a venous lumen of the catheter.

Some multilumen catheters for dialysis treatment are placed within a patient for use over extended periods of time. During such use, one or more of the catheter lumens can narrow and/or occlusive material can form on any surface of the catheter segment implanted within the body. This occlusive material can develop into a blockage developing in an opening or openings of the catheter. In some instances, blood can infiltrate lumens of the catheter despite the presence of a lock solution such as heparin. The infiltration of blood can result in lumen narrowing, occlusion and/or bacterial colonization of one or more of the catheter lumens. These issues can inhibit the proper function of the catheter, result in patient complications, and/or necessitate replacement of the catheter.

SUMMARY

In general, according to one aspect of the present disclosure, a catheter assembly includes an elongate member and a balloon. The elongate member defines at least one lumen and an outer surface. The outer surface of the elongate member defines one or more openings in fluid communication with the at least one lumen.

The balloon is disposed within the at least one lumen and is inflatable such that at least a portion of the balloon expands from the at least one lumen and through the at least one opening to increase flow restriction through the at least one opening, as compared to flow restriction through the at least one opening with the balloon in a deflated condition. The balloon is more compliant than the elongate member and has a volume that expands upon inflation. The balloon, in some embodiments, maintains a zero-fold profile in the deflated condition. In certain embodiments, the balloon is inflatable into sealing engagement with a periphery of the at least one opening. In certain embodiments, the balloon is inflatable to extend at least one of radially and distally beyond the outer surface of the elongate member.

In some embodiments, the balloon is formed of latex or polyurethane and the elongate member is formed of silicone or other biocompatible polyurethanes. In certain embodiments, the balloon is coated with one or more of an anti-thrombotic agent, an antimicrobial agent, and a biomimetic agent. The anti-thrombotic agent can comprise, for example, a base polymer layer including one or both of a biostable polymer and a bioabsorable polymer. Additionally or alternatively, the balloon can be coated with an anti-restenotic agent (e.g., paclitaxel or a -limus drug).

The catheter assembly can include a second balloon. The elongate member can define dual lumens where the balloon is a first balloon disposed within one of the lumens and the second balloon is disposed within the other lumen. In some embodiments, the elongate member includes a septum extending therethrough. The first and second balloons can be secured to the septum and inflatable through fluid communication with an inflation lumen at least partially defined by the septum.

In certain embodiments, the elongate member defines at least one distal end opening and at least one side opening. The balloon can be inflatable to restrict flow through the at least one distal end opening and/or the at least one side opening.

According to another aspect, a catheter tip assembly includes a tubular body and a balloon supported within the tubular body. The tubular body has an outer surface that defines at least one opening. The tubular body has a proximal end portion and a distal end portion. The proximal end portion of the tubular body is securable to a distal end portion of an independent catheter body.

In some embodiments, the balloon is an expandable septum. At least a portion of the expandable septum is expandable into the at least one opening. In certain embodiments, the tubular body and the expandable septum together define at least two inflation lumens and at least one external lumen. The at least one opening is in fluid communication with the at least one external lumen and the expandable septum can be inflatable through the at least two inflation lumens to expand into the at least one external lumen to restrict flow through the at least one opening.

The expandable septum, in certain embodiments, defines at least two port. Each port can be in fluid communication with a respective one of the at least two inflation lumens and each port is connectable in fluid communication to a respective internal lumen defined within a septum extending through the independent catheter body.

In some embodiments, a radio-frequency weld couples the proximal end portion of the tubular body to the distal end portion of the independent catheter body.

According to yet another aspect, a method for removing occlusive material from a catheter includes delivering inflation fluid to a balloon disposed within at least one lumen defined by an elongate member of a catheter, expanding the balloon to at least partially extend through at least one opening defined by an outer surface of the elongate member, and clearing occlusive material from the at least one opening.

Expanding the balloon can include expanding the balloon to extend one or both of radially and distally beyond the one or more openings in a direction toward an outer surface of the elongate member. The method can include occluding the at least one opening with the balloon upon inflation of the balloon. The method can include maintaining the balloon in an inflated state to prevent flow of fluid through the at least one opening.

Delivering inflation fluid to the balloon can include filling the balloon with saline until the balloon expands to a volume sufficient to clear occlusive material from the at least one opening and to completely occlude the at least one opening. The method can include deflating the balloon.

Embodiments can include one or more of the following advantages.

One or more balloons of the catheter assembly can be inflated to limit and/or prevent side slots and/or lumens of the catheter of the catheter assembly from being occluded when the catheter is positioned within a body for extended periods of time. The balloons can be inflated to completely retain lock solution within the catheter and/or increase insertablity of the catheter by increasing the stiffness of the catheter. In embodiments, the one or more balloons can be coated with an anti-thrombotic agent so that, upon inflation, the anti-thrombotic agent can be positioned in close proximity to the occlusive material to increase the effectiveness and longevity of the catheter assembly by limiting the build up of occlusive material.

The balloons of the catheter assembly are internal to the catheter and expandable through one or more openings defined by the catheter to clear an occlusion and/or to retain a lock solution. As compared to a balloon disposed on an outer surface of a catheter, the internal positioning of the balloon can reduce the catheter system profile and, in some instances, facilitate insertion of the catheter.

Other aspects, features, and advantages will be apparent from the description, drawings, and the claims.

DESCRIPTION OF THE DRAWINGS

FIG. 6A is a side view of the distal end portion of the catheter of FIG. 5A shown secured to the catheter tip assembly of FIG. 5A with the expandable septum of the catheter tip assembly shown in a deflated condition.

FIG. 6B is an end view of the catheter tip assembly shown in FIG. 6A with the expandable septum of the catheter tip assembly shown in the deflated condition.

FIG. 7A is a side view of the distal end portion of the catheter of FIG. 5A shown secured to the catheter tip assembly of FIG. 5A with the expandable septum of the catheter tip assembly shown in an inflated condition.

FIG. 7B is an end view of the catheter tip assembly shown in FIG. 7A with the expandable septum of the catheter tip assembly shown in the inflated condition.

DETAILED DESCRIPTION

Figure 1:
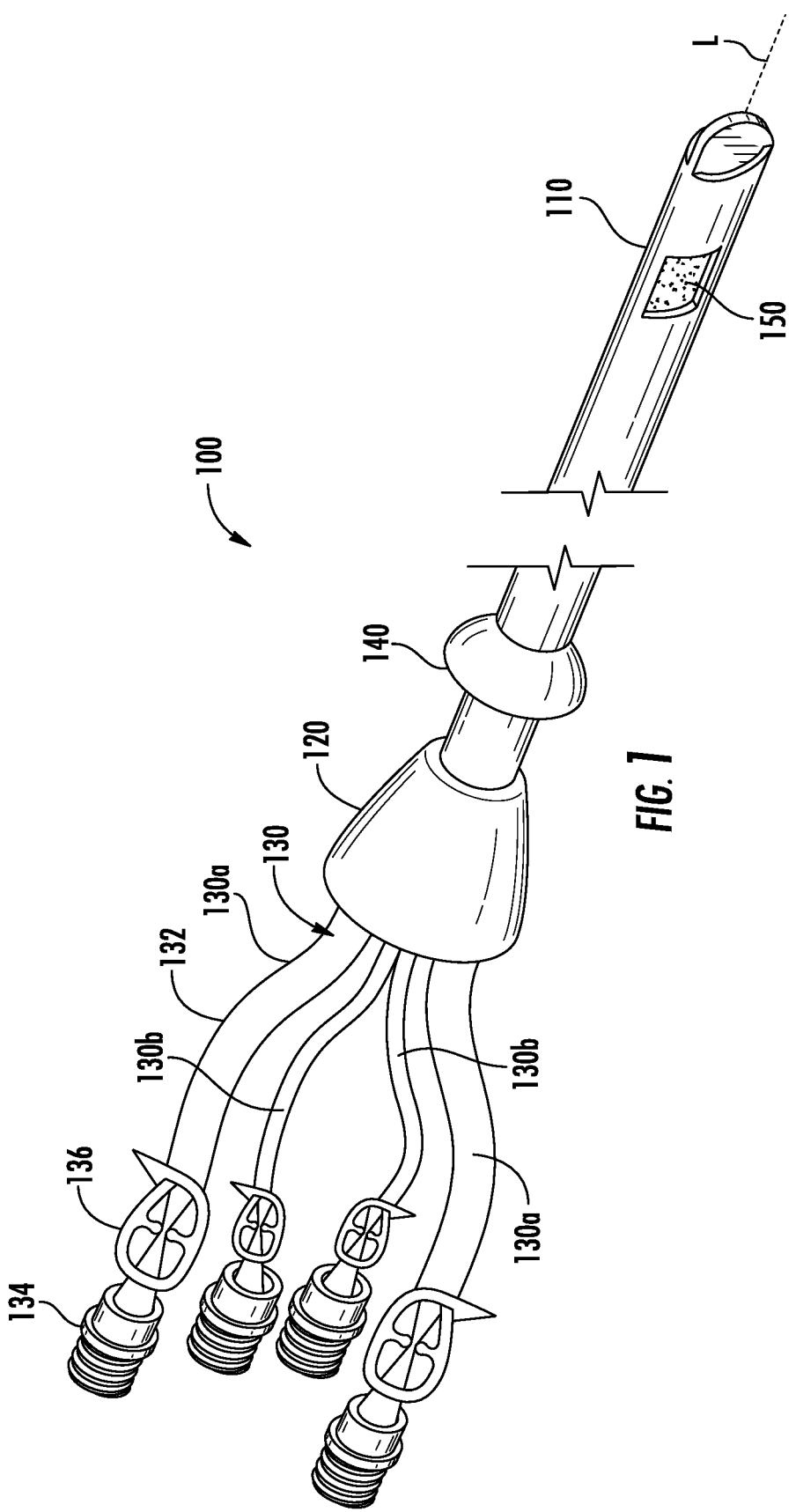
FIG. 1 is a perspective view of a catheter assembly.
Figures 2A, 2B:
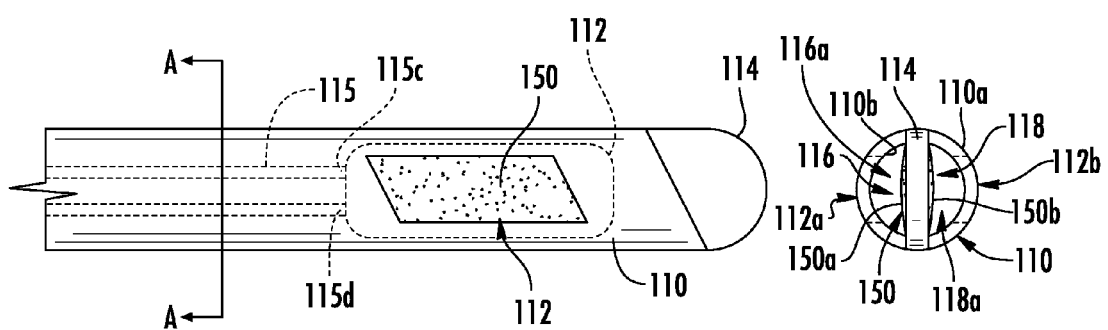
FIG. 2A is an enlarged, side view of a distal end portion of the catheter assembly shown in FIG. 1 with a balloon assembly of the catheter assembly shown in an uninflated condition.
FIG. 2B is an enlarged, end-axial view of the catheter assembly shown in FIG. 1 with the balloon assembly shown in the deflated condition.

As used herein, the term "clinician" refers to a doctor, nurse, or other care provider and may include support personnel. The terms "proximal" or "trailing" each refer to the portion of a structure closer to a clinician, and the terms "distal" or "leading" each refer to a portion of a structure farther from the clinician. As used herein, the term "subject" refers to a human patient or other animal.

Referring now to FIGS. 1, 2A-2B, and 4, a catheter assembly 100 includes an elongate member 110 that extends distally from a hub 120 and a quadruple-lumen extension tube assembly 130 that extends proximally from the hub 120. The elongate member 110 is a catheter having an outer surface 110a, an inner surface 110b, and, in some embodiments, having a tubular body. The elongate member 110 defines one or more side openings 112 and, in some embodiments, supports one or more cuffs 140. In use, as described in further detail below, the portion of the catheter assembly 100 distal to the cuff 140 is implanted within the body of a subject, and the portion of the catheter assembly 100 proximal to the cuff 140 remains outside of the body of the subject in a position accessible to a clinician. Bodily fluid (e.g., blood) can be withdrawn from the subject and/or returned to the subject through the side openings 112. As also described in further detail below, a first balloon 150a and a second balloon 150b are disposed adjacent the side openings 112 such that inflation and/or deflation of the first and second balloons 150a, 150b can remove blockage from the side openings 112 and/or can occlude the side openings 112 to hold a lock solution within the catheter assembly 100 between periods of treatment (e.g., during an interdialytic period).

The elongate member 110 can be formed of a rigid polymeric material such as silicone or other biocompatible polyurethane. The elongate member 110 includes a septum 114 extending at least the length of the elongate member and defining a longitudinal axis "L." The inner surface 110b of the elongate member 110 and side surfaces 114a of the septum 114 together define a first lumen 116 and a second lumen 118. One of the lumens 116, 118 can function as an arterial lumen and the other of the lumens 116, 118 can function as a venous lumen during a dialysis procedure. The first lumen 116 includes a first distal end opening 116a, and the second lumen 118 includes a second distal end opening 118a.

The one or more side openings 112 can include a first side opening 112a in fluid communication with the first lumen 116 and a second side opening 112b in fluid communication with the second lumen 118. A first balloon 150a is adjacent the first side opening 112a and the second balloon 150b is adjacent the second side opening 112b communicating with the second lumen 118. Each side opening 112a, 112b can have geometric shapes including polygonal configurations, circular configurations, and/or combinations thereof.

The septum 114 defines one or more inflation lumens 115 extending at least axially along the length of the septum 114, from the hub 120 to the balloons 150a, 150b. The one or more inflation lumens 115 can include, for example, a first inflation lumen 115a and a second inflation lumen 115b. The first and second inflation lumens 115a, 115b are positionable in fluid communication with an inflation source such as, for example, a syringe pre-filled with an inflation fluid (e.g., saline). It should be appreciated that the inflation lumen can be formed, for example, during the extrusion of the elongate member 110.

The septum 114 supports the first and second balloons 150a and 150b. The first balloon 150a can be mounted to one side of the septum 114, and the second balloon 150b can be mounted on the opposite side of the septum 114. It should be appreciated that the first and second balloons 150a, 150b can each be mounted to respective sides of the septum 114 using, for example, adhesives. Each of the interiors of the balloons 150a and 150b is in fluid communication with one or both of the inflation lumens 115a, 115b through one or more ports 115c, 115d defined at respective ends of the inflation lumens 115a, 115b. The ports 115c, 115d may extend through or terminate within the interior of the respective balloons 150a, 150b. The balloons 150a, 150b are inflatable from a deflated condition to an inflated condition upon receiving inflation fluid from the inflation source.

In the deflated condition, each balloon 150a, 150b is supported by the septum 114 to permit substantially unrestricted fluid communication through the respective lumen 116, 118, the respective side opening 112a, 112b, and/or the respective distal end opening 116a, 118a. The balloons 150a, 150b, in some embodiments, can maintain a zero-fold profile in the deflated condition. In some embodiments, the balloons 150a, 150b are at least partially recessed within the septum 114.

In the inflated condition, each balloon 150a, 150b is inflated to a volume within the respective lumen 116, 118 sufficient to at least partially restrict fluid flow through the respective lumen 116, 118, the respective side opening 112a, 112b, and/or the respective distal end opening 116a, 118a. In certain embodiments, the balloons 150a, 150b can be inflated into sealing engagement with the inner surface 110b of the elongate member 110 (e.g., upstream of the respective side openings 112a, 112b). In some embodiments, each balloon 150a, 150b can be inflated to occlude completely the respective side opening 112a, 112b and/or the respective distal end opening 116a, 116b. As shown in FIGS. 2A-3B, for example, the balloons 150a, 150b expand in a radial and/or axial direction and can be inflated to extend radially and/or distally through the respective side opening 112a, 112b and/or the respective distal end opening 116a, 118a and extend outwardly of the outer surface 110a of the elongate member 110. The balloons 150a, 150b can be arranged to be independently inflatable or simultaneously inflatable. Moreover, it should be appreciated that, as used herein, the term balloon refers to any structure defining a volume and expandable upon introduction of fluid into the volume and, thus, can include a unitary arrangement of material and/or a multi-component arrangement secured together to form, for example, a bladder.

The balloons 150a, 150b can be produced using one or more of molding, blowing, dipping, and extruding. The balloons 150a, 150b can be formed of a very compliant, low durometer material with high elastomeric/low fatigue properties. Balloons with such properties can be achieved through material selection and/or balloon dimensions (e.g., wall thickness). The elongate member 110 can be formed of one or more materials exhibiting less compliant and higher durometer properties than those of the balloons 150a, 150b such that the expanded balloons 150a, 150b deform to fill the respective side opening 112a, 112b and/or the respective distal end opening 116a, 118a.

Figures 3A, 3B:
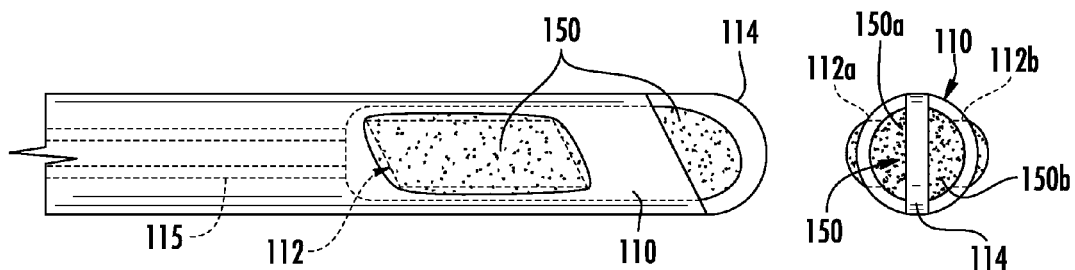
FIG. 3A is an enlarged, side view of the distal end portion of the catheter assembly shown in FIG. 1 with the balloon assembly shown in an inflated condition.
FIG. 3B is an enlarged, end-axial view of the catheter assembly shown in FIG. 1 with the balloon assembly shown in the inflated condition.
Figure 4:
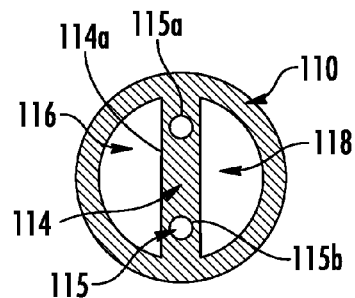
FIG. 4 is an enlarged, cross-sectional view taken along line A-A of FIG. 2A.
Figure 5A:
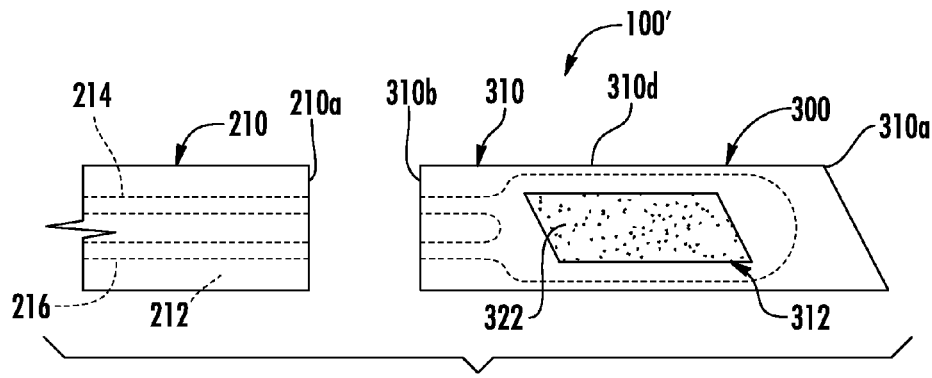
FIG. 5A is a side view of a distal end portion of a catheter and a catheter tip assembly.
Figure 5B:
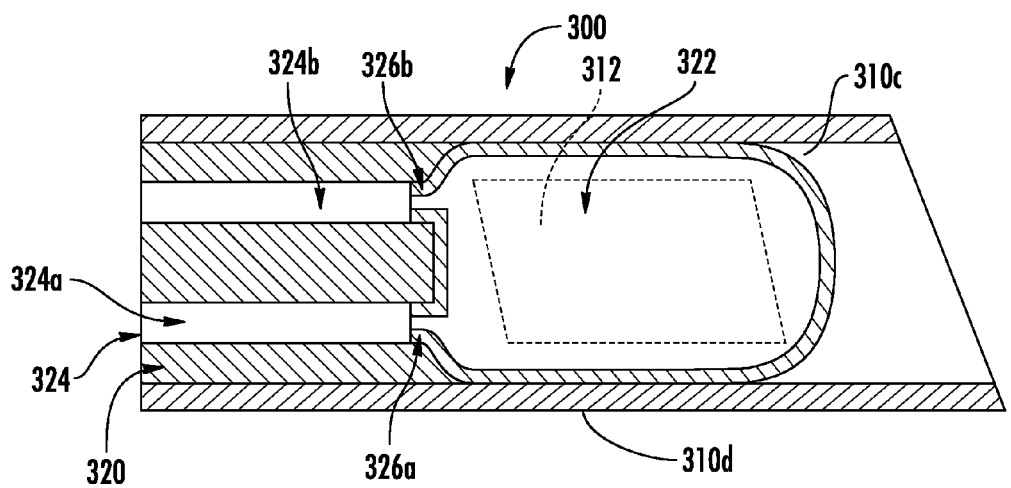
FIG. 5B is a cross-sectional view of the catheter tip assembly shown in FIG. 5A.

The balloons 150a, 150b can be formed of a compliant material (e.g., one or more of latex, polyurethane, and silicone) to facilitate radial expansion and/or axial expansion in response to introduction of inflation fluid into the balloons 150a, 150b to move the balloons 150a, 150b from the deflated condition (FIGS. 2A and 2B) to the inflated condition (FIGS. 3A and 3B). Similarly, it should be appreciated that the withdrawal of inflation fluid from the balloons 150a, 150b can result in movement of the balloons 150a, 150b from the inflated condition to the deflated condition.

The extension tube assembly 130 includes a plurality of treatment extension tubes 130a and inflation extension tubes 130b. Each treatment extension tube 130a is in fluid communication with one of the lumens 116, 118, and each inflation extension tube 130b is in fluid communication with one of the inflation lumens 115a, 115b. While two treatment extension tubes and two inflation extension tubes are shown, additional treatment lumens and/or additional inflation lumens are possible. For example, three or more treatment extension tubes can be in fluid communication with a corresponding number of lumens and three or more inflation extension tubes can be in fluid communication with a corresponding number of inflation lumens.

Each extension tube 130a, 130b includes an elongate body portion 132 extending proximally from the hub 120. A luer adapter 134 is secured to a proximal end portion of each elongate body portion 132 and supports a clamp 136 between the luer adapter 134 and the hub 120. Each luer adapter 134 is connectable, for example, to a hemodialysis machine (not shown) and/or the inflation source (not shown) and/or any device with a standard luer-taper/conical fitting such as fittings specified in ISO 594. The clamp 136 is movable between clamped and unclamped positions about the elongate body portion 132 to control fluid flow through the elongate body portion 132. In the clamped position, the clamp 136 substantially restricts (e.g., prevents) fluid flow through the elongate body portion 132 and, in the unclamped position, the clamp 136 permits substantially unrestricted fluid flow through the elongate body portion 132.

In an exemplary use, the catheter assembly 100 is inserted into a subject. The luer adapters 134 of the treatment extension tubes 130a are secured to a treatment device (e.g., hemodialysis machine and the clamps 136 are moved to the unclamped position to permit flow of a bodily fluid (e.g., blood flow) through the treatment extension tubes 130a as part of a medical procedure (e.g., hemodialysis). After completion of the medical procedure, a lock solution (e.g., a solution including heparin) can be introduced into the lumens 116, 118 of the catheter assembly 100, and the clamps 136 can be moved to the clamped position to restrict flow through the treatment extension tubes 130a. The luer adapters 134 of the treatment extension tubes 130a can be disconnected from the treatment device, and a syringe or other inflation source can be secured to the inflation extension tube(s) 130b to inject the inflation fluid into one or both of the balloons 150a, 150b such that the balloons 150a, 150b inflate to obstruct flow through the side and/or distal end openings of the elongate member 110. The extension of the inflated balloons 150a, 150b through the side openings 112 and/or through the distal openings 116a, 118a can reduce the likelihood of (e.g., prevent) occlusive material build-up and/or bacterial colonization within the elongate member 110, each of which can result from in vivo catheter placement for extended periods, such as those associated with chronic hemodialysis catheters (e.g., about 30 days or more).

To deflate the balloons 150a, 150b, for example, to perform another medical procedure, a syringe or other fluid removal source may be connected to one of the inflation extension tubes 130b to provide suction sufficient to withdraw the inflation fluid from within the balloons 150a, 150b. A desired amount of inflation fluid can be purged from the balloons 150a, 150b for whole or partial deflation of the balloons 15a, 150b. In some embodiments, the inflation lumens 115a, 115b allow bi-directional flow from and to the balloons 150a, 150b. Alternatively or additionally, the balloons 150a, 150b can be inflated and/or re-inflated to clear occlusive material formed on or near the side openings 112a, 112b and/or distal end openings 116a, 116b of the elongate member 110.

While certain embodiments have been described, other embodiments are possible.

For example, while the balloon assembly 150 has been described as including two balloons, other embodiments are additionally or alternatively possible. In some embodiments, the balloon assembly includes a single balloon. The single balloon, upon inflation, can expand from the septum 114 in a direction transverse to the longitudinal axis "L" and into one or both of the external lumens 116, 118. In use, one lumen is used to inject fluid while the other lumen is used to purge contents and ensure complete charging of fluid.

As another example, while the catheter assemblies have been described as having a unitary construction, other embodiments are additionally or alternatively possible. For example, with reference to FIGS. 5A-5B, 6A-6B, and 7A-7B, a catheter assembly 100' includes a separate catheter 210 and a catheter tip assembly 300. The elongate member 210 is a catheter having a distal end portion 210a and a septum 212 extending through the elongate member 210 along the axial length of the elongate member 210. The septum 212 defines a first inflation lumen 214 and a second inflation lumen 216 (shown in phantom), each extending to the distal end portion 210a of the elongate member 210.

The catheter tip assembly 300 includes an elongate tubular body 310 having a proximal end portion 310b and a distal end portion 310a. The elongate tubular body 310 has an inner surface 310c and an outer surface 310d. The elongate tubular body 310 defines one or more side openings 312 extending from the outer surface 310d to the inner surface 310c. The elongate tubular body 310 includes a septum 320 extending at least partially along an axial length of the tubular body 310. In certain embodiments, the septum 320 extends the entire length of the elongate tubular body 310 and is formed of a compliant and expandable material to facilitate expansion of the entire septum 320 along the length of the elongate tubular body 310.

The septum 320 defines inflation lumens 324 including a first inflation lumen 324a and a second inflation lumen 324b. The septum 320 includes a balloon 322 connected to a distal end portion of the septum 320 and in fluid communication with the first and second inflation lumens 324a, 324b. The first and second inflation lumens 324a, 324b include respective first and second ports 326a, 326b establishing fluid communication between the first and second inflation lumens 324a, 324b and the balloon 322. A portion of the side surfaces 322a, 322b of the balloon 322 is secured to the inner surface 310c of the elongate tubular body 310, and a proximal end portion of the balloon 322 can be secured adjacent the first and second ports 326a, 326b. Each of the inflation lumens 324 is dimensioned to permit passage of inflation fluid to inflate and/or deflate the balloon 322. In certain embodiments, the inflation lumens 324 permit bi-directional flow such that inflation fluid moves to the balloon 322 through one of the inflation lumens 324 and an overflow of inflation fluid moves from the balloon 322 through another one of the inflation lumens 324.

The proximal end portion 310b of the catheter tip assembly 300 is secured to the distal end portion 210a of the tubular body 210. For example, the catheter tip assembly 300 can be welded to the tubular body 210, such as with radio-frequency energy, along a weld line 250. Additionally or alternatively, the catheter tip assembly 300 can be over-molded onto the tubular body 210.

With the catheter tip assembly 300 and the tubular body 210 connected, the first and second inflation lumens 324a, 324b are in fluid communication with the first and second inflation lumens 214, 216 of the elongate member 210. Further, the connection of the catheter tip assembly 300 and the tubular body 210 creates a single septum defined by the septum 212 of the elongate member 210, the septum 320 of the tubular body 310, and the balloon 322 of the tubular body 310. As shown in FIG. 6B, the inner surfaces of the single elongate assembly, together with the septum 212 of the elongate member 210 and the septum 320 of the tubular body 310, define first and second lumens 330, 340 on opposite sides of the single septum 320.

With specific reference to FIGS. 7A and 7B, the expandable portion 322 is inflatable to completely occlude the side openings 312a, 312b and/or the respective distal end openings 330a, 340a. Similarly, the expandable portion 322 is inflatable to extend radially and/or distally through the side openings 312a, 312b and/or through the distal end openings 330a, 340a from or beyond the outer surface 310d of the tubular body 310.

Figure 8:
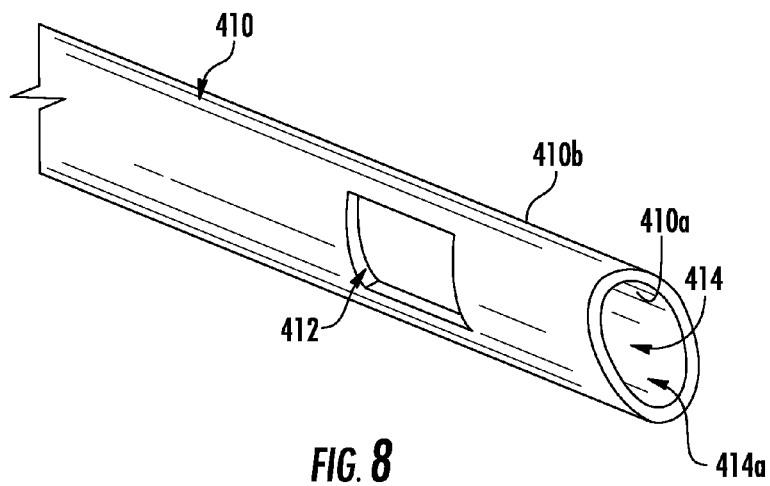
FIG. 8 is a perspective view of a distal end portion of another catheter assembly.
Figure 9A:
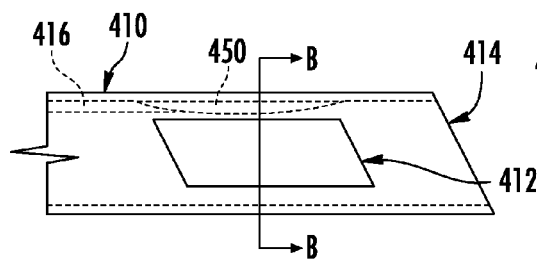
FIG. 9A is an enlarged, side view of the distal end portion of the catheter assembly of FIG. 8 with a balloon of the catheter assembly being shown in a deflated condition.
Figure 10A:
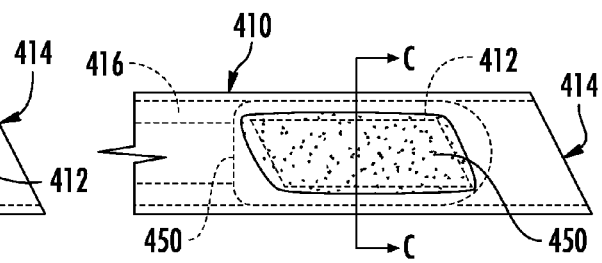
FIG. 10A is an enlarged, side view of the distal end portion of the catheter assembly of FIG. 8 with the balloon of the catheter assembly being shown in an inflated condition.
Figure 9B:
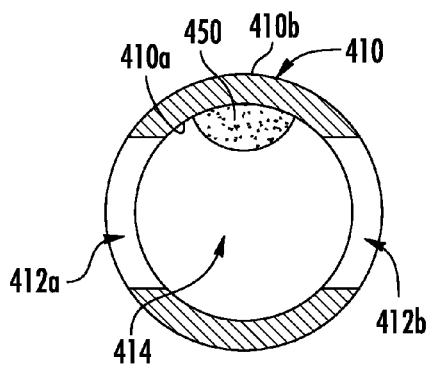
FIG. 9B is an enlarged, cross-sectional view taken along line B-B shown in FIG. 9A.
Figure 10B:
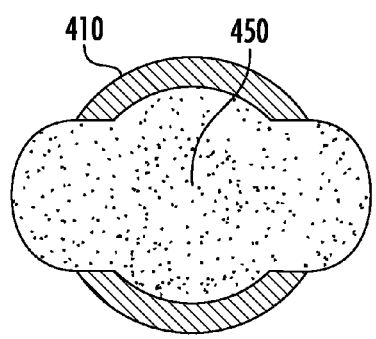
FIG. 10B is an enlarged, cross-sectional view taken along line C-C shown in FIG. 10A.

As still another example, catheter assemblies have been described as including multilumen catheters having a septum at least partially defining in each lumen. However, other lumen arrangements are additionally or alternatively possible. For example, as seen in FIGS. 8 and 9A-9B, a catheter 410 is an elongate tubular body having an inner surface 410a and an outer surface 410b. The inner surface 410a defines a lumen 414 terminating at a distal end opening 414a. The tubular body 410 defines one or more side openings 412 extending from the outer surface 410b to the inner surface 410a. The one or more side openings 412 can include a first side opening 412a and a second side opening 412b.

The elongate tubular body 410 supports a balloon 450 and defines an inflation lumen 416 in fluid communication with the balloon 450. The balloon 450 is secured to the inner surface 410a of the elongate tubular body 410 at a position proximal to a distal end portion of the elongate tubular body 410 and adjacent the side openings 412. As shown in FIG. 9B, for example, the balloon 450 can be between the side openings 412a, 412b in a direction transverse to the catheter 410. The inflation lumen 416 is defined by the elongate tubular body 410.

In use, the balloon 450 is inflated to partially and/or completely occlude one or both of the side openings 412a, 412b and/or the lumen 414 while the distal end portion of the balloon 450 is proximal to the distal end opening 414a. In embodiments, the balloon 450 can be inflated to extend radially and/or distally through the side openings 412a, 412b and/or the distal end opening 414a of the tubular body 410.

As still another example, any of the balloons described herein can be coated with an anti-thrombotic or anti-microbial agent. In some embodiments, the anti-thrombotic agent is heparin or p-selectin. In certain embodiments, the anti-thrombotic agent includes a base polymer layer having a biostable polymer (phosphorylcholine, for example) and/or a bioabsorbable polymer (examples include PLA, PGA, PLLA). With the anti-thrombotic agent coated on the balloons, the anti-thrombotic agent can be continuously delivered by the inflated balloons to the side and/or distal end openings to limit and/or prevent the build up of occlusive material such as thrombus that may develop during prolonged in vivo usage of chronic catheters. In some embodiments, the anti-microbial agent is one or more of chlorhexidine, silver, and benzalkonium chloride. The anti-microbial agent can be impregnated within the balloon and/or within the elongate member. Additionally or alternatively, the anti-microbial agents can be encapsulated within a polymer matrix coated on the elongate member. In certain embodiments, the elongate member and/or balloon material is produced using polyurethane and biomimetic technology, reducing the need for anti-thrombogenic material and/or anti-microbial material while performing a similar function.

As yet another example, while catheter assemblies have been described as used in hemodialysis procedures, the use of catheter assemblies in other medical procedures is additionally or alternatively possible. For example, catheter assemblies can be used in procedures requiring localized drug delivery and/or in peritoneal dialysis.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A catheter assembly, comprising:
   an elongate member defining a catheter body having at least one lumen, an outer surface of the elongate member defining at least one distal end opening and at least one side opening, the at least one distal end opening and the at least one side opening being in fluid communication with the at least one lumen; and
   a balloon disposed within the at least one lumen, the balloon being inflatable such that at least a portion of the balloon expands from the at least one lumen and through the at least one distal end opening and the at least one side opening to increase flow restriction through each of the at least one distal end opening and the at least one side opening as compared to flow restriction through the respective distal end opening and side opening with the balloon in a deflated condition.

2. The catheter assembly of claim 1, wherein the balloon is more compliant than the elongate member.

3. The catheter assembly of claim 2, wherein the balloon is formed of latex or polyurethane and the elongate member is formed of silicone or polyurethane.

4. The catheter assembly of claim 1 wherein the balloon is a compliant balloon with a volume that expands upon inflation.

5. The catheter assembly of claim 1, wherein the balloon is inflatable into sealing engagement with a periphery of the at least one distal end opening and the at least one side opening.

6. The catheter assembly of claim 1, wherein the balloon is inflatable to extend at least one of radially and distally beyond the outer surface of the elongate member.

7. The catheter assembly of claim 1, further comprising a second balloon, wherein the elongate member defines dual lumens, the balloon is a first balloon disposed within one of the lumens and the second balloon is disposed within the other lumen.

8. The catheter assembly of claim 7, wherein the elongate member includes a septum extending therethrough, the first and second balloons being secured to the septum and inflatable through fluid communication with an inflation lumen at least partially defined by the septum.

9. The catheter assembly of claim 1, wherein the balloon maintains a zero-fold profile in the deflated condition.

10. The catheter assembly of claim 1, wherein the balloon is coated with one or more of an anti-thrombotic agent, an anti-microbial agent, and a biomimetic agent.

11. The catheter assembly of claim 10, wherein the anti-thrombotic agent comprises a base polymer layer including at least one of a biostable polymer and a bioabsorbable polymer.

* * * * *